United States Patent [19]

Hillstead

[11] Patent Number: 4,895,565
[45] Date of Patent: * Jan. 23, 1990

[54] MEDICAL INSTRUMENT VALVE

[75] Inventor: Richard A. Hillstead, Hollywood, Fla.

[73] Assignee: Cordis Corporation, Miami Lakes, Fla.

[*] Notice: The portion of the term of this patent subsequent to Jan. 17, 2006 has been disclaimed.

[21] Appl. No.: 194,539

[22] Filed: May 16, 1988

Related U.S. Application Data

[63] Continuation-in-part of Ser. No. 99,139, Sep. 21, 1987, Pat. No. 4,798,594.

[51] Int. Cl.$^4$ .............................................. A61M 25/00
[52] U.S. Cl. ................................... 604/167; 604/256; 137/849; 251/149.1
[58] Field of Search ............... 604/167, 169, 247, 256, 604/237, 265; 137/846, 849; 251/149.1

[56] References Cited

U.S. PATENT DOCUMENTS

| | | |
|---|---|---|
| 3,313,299 | 4/1967 | Spademan . |
| 3,853,127 | 12/1974 | Spademan . |
| 4,000,739 | 1/1977 | Stevens . |
| 4,073,297 | 2/1978 | Kopp . |
| 4,109,836 | 8/1978 | Falarde . |
| 4,177,814 | 12/1979 | Knepshield et al. . |
| 4,338,934 | 7/1982 | Spademan . |
| 4,421,296 | 12/1983 | Stephens . |
| 4,424,833 | 1/1984 | Spector et al. . |
| 4,430,081 | 2/1984 | Timmermans . |
| 4,436,519 | 3/1984 | O'Neill . |
| 4,576,595 | 3/1986 | Aas et al. . |
| 4,610,665 | 9/1986 | Matsumoto et al. . |
| 4,610,674 | 9/1986 | Suzuki et al. . |
| 4,626,245 | 12/1986 | Weinstein .............................. 604/167 |
| 4,629,450 | 12/1986 | Suzuki et al. . |
| 4,649,904 | 3/1987 | Krauter et al. .................. 604/167 X |
| 4,653,477 | 3/1987 | Akui et al. . |
| 4,655,752 | 4/1987 | Honkanen et al. . |
| 4,673,393 | 6/1987 | Suzuki et al. . |
| 4,674,496 | 6/1987 | Svadjian et al. . |
| 4,752,287 | 6/1988 | Kurtz et al. ..................... 604/256 X |

*Primary Examiner*—Stephen C. Pellegrino
*Attorney, Agent, or Firm*—Gerstman & Ellis, Ltd.

[57] ABSTRACT

A hemostasis valve is provided for catheters or the like, comprising an elastomeric partition valve secured in a housing. A linear slit extends through the partition valve between the major faces thereof. By this invention, the partition of the valve has at least one concave face through which the slit extends. Such a partition valve provides further improved sealing characteristics over a wide range of diameters of catheters, leads, or the like penetrating the partition valve, particularly reducing frictional resistance to catheter advancement and rotation through the valve and also reducing catheter collapse in the valve.

21 Claims, 1 Drawing Sheet

U.S. Patent    Jan. 23, 1990    4,895,565
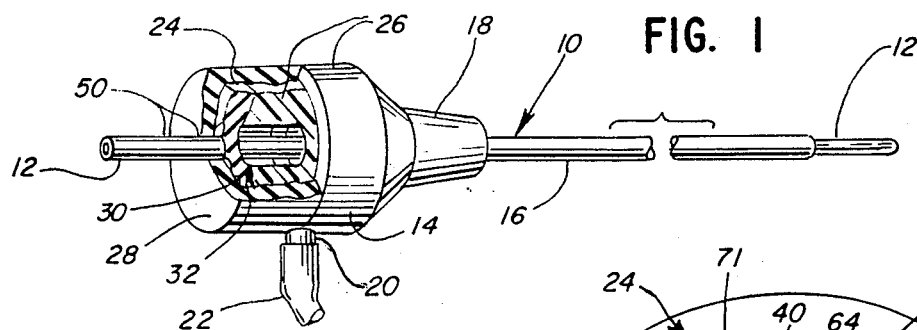
FIG. 1
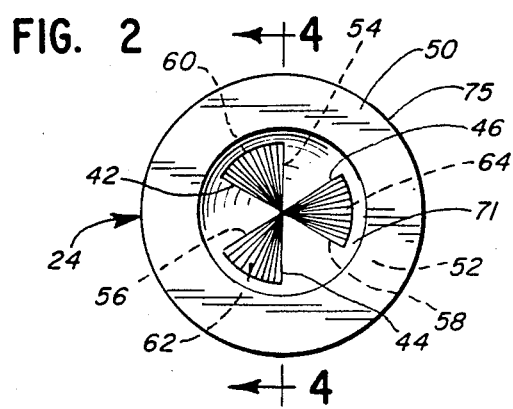
FIG. 2
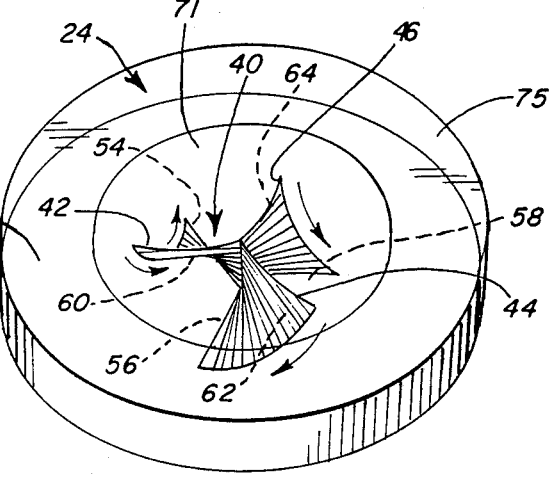
FIG. 3
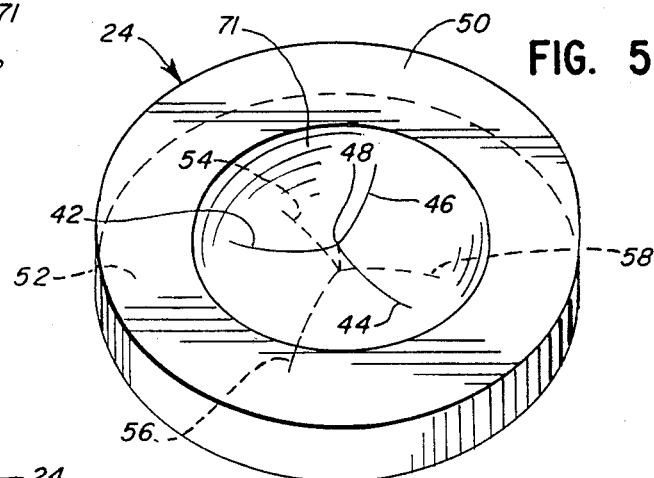
FIG. 5
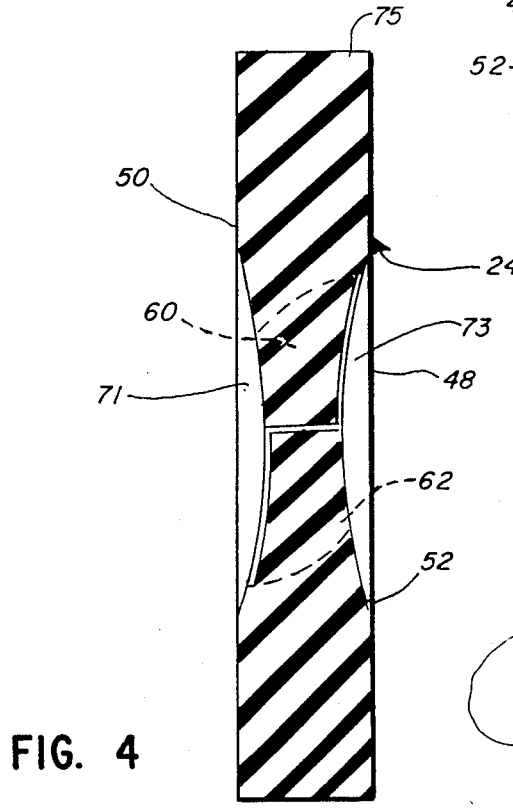
FIG. 4
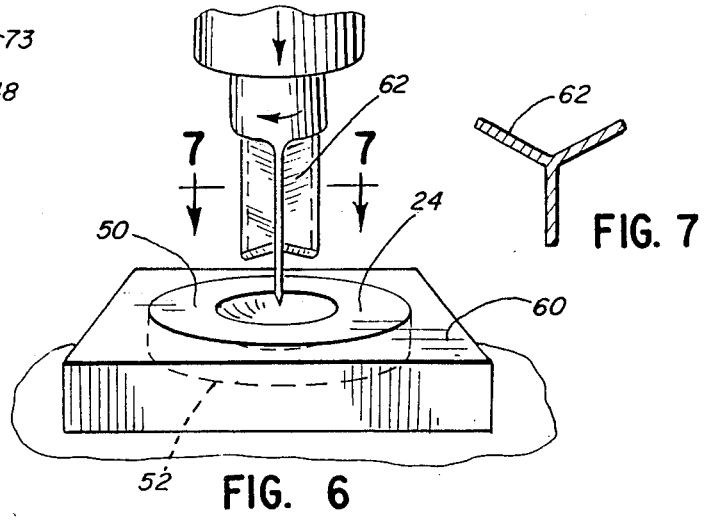
FIG. 6
FIG. 7

MEDICAL INSTRUMENT VALVE

CROSS REFERENCE TO RELATED APPLICATION

This application is a continuation-in-part of U.S. application Ser. No. 099,139, filed Sept. 21, 1987, now U.S. Pat. No. 4,798,594.

BACKGROUND OF THE INVENTION

Hemostasis valves are well-known, being currently used, for example, on catheters for performing percutaneous transluminal coronary angioplasty (PTCA) as well as angiographic procedures, for example where x-ray contrast fluid is inserted into the coronary artery. Hemostasis valves are also used to prevent the leakage of blood out of the ends of dilitation and guidance catheters, to prevent the seepage of blood between the guide wire and the dilitation catheter, and also between the two catheters.

Numerous types of hemostasis valves are known, by way of example, see Stevens, U.S. Pat. No. 4,000,739, Matsumoto et al, U.S. Pat. No. 4,610,665, and Weinstein U.S. Pat. No. 4,626,245.

Hemostasis valves may also be employed for the introduction of other catheters into the circulatory system or elsewhere in a leak-proof manner. The valve may be carried by any catheter or sheath introducer, to permit an inner catheter, probe, or the like to be placed through the hemostasis valve to form a leak-proof seal and a port of entry.

In accordance with this invention, a hemostasis valve is provided which exhibits significantly improved tolerance for varying diameters of catheters, probes, leads or the like penetrating it without leakage or damage to the valve. While the valve of this invention exhibits improvements by reducing sliding and rotational resistance for elongated objects such as catheters as they pass through the valve, they still provide good resistance to dislodgement of such a catheter after it has been properly positioned. Similarly, reduced compression on the catheter or other elongated member is noted within the valve of this invention, permitting greater facility in the use of multi-lumen catheters, for example, and avoiding collapse of thin-walled catheters at the point where they extend through the valve. Nevertheless, the hemostasis valve of this invention still exhibits excellent pressure handling capabilities, to prevent leakage under pressure, whether or not an elongated object is passing through the valve of this invention.

DESCRIPTION OF THE INVENTION

This invention relates to a hemostasis valve which may be used for preventing backflow of blood or other fluids through a catheter or the like, while permitting passage of a probe, an inner catheter, an electrical lead, or any other elongated member through the valve. As in conventional, the hemostasis valve comprises an elastomeric partition member having opposed major faces, the petition member being secured in a housing. A linear slit extends through the partition member between the major faces thereof.

In accordance with this invention, at least one of the major faces defines a concave surface to reduce the central thickness of the partition member. The slit extends through the concave surface. Preferably, both of the major faces of the partition member are concave in shape.

The effect of this to reduce the thickness of the elastomeric material around the slit, which has the effect of reducing the frictional resistance against a catheter passing through the slit or rotating therein. Additionally, the overall inward pressure exerted on the catheter by the elastomeric material of the partition, at the point where the catheter penetrates it, is reduced, which permits the use of thinner walled catheters, when compared with equivalent partition members of the same design which do not have concave major faces.

Not only is there better lubricity or sliding feel of the catheter as it is advanced and retracted through the partition member, but the torquability or rotational resistance is reduced for catheters which are to be rotated for steering purposes or the like.

As a further advantage, the valve of this invention with concave-faced partitions is somewhat self-compensating in that a catheter of larger outer diameter will encounter at its outer edge more material of the partition member as a consequence of the concave shape of the face or faces. Thus, larger catheters will encounter a stronger seal of greater thickness and mass at the junction between the outer diameter of the catheter and the material of the partition member about the slit, which is deemed desirable in most circumstances. As an additional advantage, the periphery of the partition member is thicker than central portions because of the concave shape of the major face or faces, so that the partition can be firmly secured in a peripheral pressure seal, despite the thinner nature of the central portions.

Preferably, the slit defines a first line on a first major face and a second line on the second major face of the partition member. The first line and the second line each have a similar configuration which may be a branched configuration, but are in rotational non-alignment with each other. Preferably, a generally helical slit section extends between the first line and the second line through the partition member. Such a design of slit has been found to provide improved sealing characteristics over a wide range of catheter diameters (or diameters of other elongated members passing through the hemostasis valve). Additionally, a self compensating lubricity is provided, possibly caused by a sliding "iris" effect inherent in the spiral design of the slit preferably used in the hemostasis valve of this invention, to permit easy insertion and withdrawl of elongated members through the valve. Nevertheless, the structure provides sufficient gripping action so that elongated members are not easily dislodged by unintentional means.

Additionally, the design of slit in the valve of this invention provides reduced compression on multi-lumen or thin-walled catheters, as well as improved resistance to leakage under circumstances of high pressure while avoiding catheter collapse. The valve of this invention is easily manufactured for significant improvements in the performance of hemostasis valves for the above reasons and others as well.

Preferably, the above described line at each major face of the partition member defines a plurality of intersecting radii, typically three, the radii being preferably substantially equiangularly spaced to each other on each face. These radii are non-aligned (i.e., they define an angle) with corresponding radii on the opposed major face, with the respective, corresponding, opposed radii on opposed major faces defining a plurality (typically three) of the helical slit sections between them, the helical slit sections being in generally coaxial relation to one another.

Typically, the respective lines or radii on the opposed major faces which are connected to each other by a helical slit section define an angle of 10 to 180 degrees or more. Preferably this angle is 30 to 90 degrees, more preferably about 60 degrees.

The housing and elastomeric partition may be of any conventional design in which the housing holds the elastomeric partition about its edges, so that the central portion of the major faces are exposed for access by a catheter, a probe, or the like for passage therethrough. The elastomeric partition member may be a simple disc of natural or synthetic latex, or any other desired elastomer which generally has sufficient resilience, typically in the range of 30 to 50 Shore "A" Durometer. Interestingly, inherently good needle resealability may not necessarily be a critical characteristic for a good material used as the elastomeric partition valve in this invention. For example, silicone rubber, especially silicone rubber materials having an impregnated amount of free silicone fluid (e.g. dimethylpolysiloxane preferably present in an amount of 2 to 10 weight percent) may desirably be used, although such is not often used as a needle-resealable barrier. The free silicone fluid can act as a lubricant that facilitates the advantages of this invention. Other elastomers and other impregnated fluid lubricants may also be used.

As one manufactures the partition member in accordance with this invention by cutting a slit through it, one may rotate the cutting blade (or the valve) during the cutting process so that the blade at its entry point on one major face defines an angle with itself at its exit point on the other major face, to provide the desired helical slit as described above.

The cutting blade may be of the desired helical shape, being rotated as it cuts through the elastomeric partition valve, but straight blades, perpendicular to the plane of the partition valve, can also be easily used because of the elastomeric nature of the partition member. Specifically, the shape of the blade at its cutting edge will be identical to the shape of the slit at each major face. Thus, preferably, the blade may also comprise a plurality of intersecting radial edges, particularly three intersecting, substantially equiangularly spaced radial edges, to define the preferred slit pattern. Then, the radially edged blades pass through the elastomeric valve with rotation to form the desired angle between the lines of radii at each major face as described above. It is generally preferred for a slit having a cross section of chevron shape, or a shape of two to six substantially equiangularly spaced radii from a common origin, to be used. However, it is not mandatory for the radii to be equiangular in their spacing.

Also, other slit designs may be used in accordance with this invention as may be desired. For example, a slit design as covered by Weinstein U.S. Pat. No. 4,626,245 may desirably be used, or any other known slit configuration for the partition member of a slit-type partition valve.

After the slit has been formed by cutting into the elastomeric partition member of this invention, it may be mounted into a housing in conventional manner, carried if desired on a catheter or the like for use. See the above cited patents, as well as other known technology for conventional housing designs and the like.

DESCRIPTION OF THE DRAWINGS

In the drawings,

FIG. 1 is a perspective view, with a portion cut away, for a catheter which carries the hemostasis valve of this invention.

FIG. 2 is an enlarged, plan view of the partition member used in the hemostasis view of FIG. 1 showing a preferred slit pattern in the elastomeric partition member.

FIG. 3 is a perspective view of the elastomeric partition member of FIG. 2, showing the slit pattern.

FIG. 4 is a transverse sectional view taken along line 4—4 of FIG. 2.

FIG. 5 is a perspective view of the elastomeric partition member of FIG. 2.

FIG. 6 is a partial perspective view of a device for cutting the preferred slit pattern into an elastomeric disc.

FIG. 7 is a sectional view taken along line 7—7 of FIG. 6.

DESCRIPTION OF SPECIFIC EMBODIMENT

Referring to the drawings, FIG. 1 shows a catheter sheath introducer 10, adapted to receive an inner catheter 12 as shown for inserting into the vascular system of a patient. Catheter sheath introducer 10 is used to introduce a catheter into a blood vessel while preventing blood backflow along the outside surface of the catheter during procedures in which a catheter is inserted into the vessel. Current designs of catheter sheath introducers are typically limited to a narrow range of only one or two French sizes of inner catheter 12 for which they can provide effective entry and sealing, while permitting inner catheter 12 to remain lubricious by not removing too much lubricant from it. This situation is improved by the invention of the previously cited U.S. Pat. No. 4,626,245. However, in accordance with this invention, further improvements relating to size tolerance of the valve of this invention are provided, along with the other advantages as described above.

Catheter sheath introducer 10 defines outer tubular housing 14 which carries cannula portion 16 of catheter sheath introducer 10, positioned in attached, telescoping relation with tubular protrusion 18 of the housing. Side port 20 may be of conventional design, being adapted for telescoping connection with plastic tubing 22, for providing a saline solution for flushing the interior of housing 14 and tubing extension 16.

Housing 14 also carries self-sealing penetrable barrier as elastomeric partition valve member 24, which may be made of an appropriate elastomeric material. For example, natural rubber latex is well-known for providing excellent resealing characteristics. However, silicone elastomers, fluoropolymers, polyurethane elastomers, or any other elastomeric material may be used, depending upon the performance parameters desired, especially when they carry an impregnating lubricating oil. Preferably an oil-impregnated silicone rubber of Durometer 40 may be used.

Housing 14 may comprise casing portions 26, 28 which are sealed together in telescopic relation and which peripherally capture penetrable barrier 24 between them as shown. Alternatively, casing portion 28 may be a screw cap, for adjustable compressive retention of elastomeric barrier 24. Annular ribs 30, 32 may be provided in each housing portion to provide more positive capture of the elastomeric portion 24.

Referring to FIGS. 2 thru 5, details of the slit design in partition member 24 are disclosed. Specifically, the cross-sectional shape of slit 40 is of the shape of three, intersecting, substantially equiangularly spaced radii 42, 44, 46, spaced about origin line 48 by about 120 degrees, and defined on major face 50. Alternatively, with four equiangularly spaced radii, the included angle between each radius is 90 degrees. Six spaced radii may define included angles of 60 degrees. Two equiangularly spaced radii define an included angle with each other of 180 degrees, and thus define a single, straight line, for a simplified version of the invention of this application.

On major face 52, on the other side of partition member 24, slit 40 defines a substantially identical cross-section of three, intersecting, substantially equiangularly spaced radii 54, 56, 58, with respective helical slit sections 60, 62, 64 defined between the respective radii on opposed faces 50, 52 through the material of partition member 24. As stated before, such a slit can be provided by a knife of corresponding cross-sectional shape which may have angled, or helical blades if desired, and which may be rotated as the blades cut through partition member 24. Specifically, the total angle of cutting rotation shown is about 60 degrees, so that each radius 42, 44, 46 on surface 50 defines an angle of about 60 degrees to each radius 54, 56, 58 on surface 52 of partition member 24. Preferably, the angle of cutting rotation increases linearly as cutting progresses. For example, if the total cutting angle is 60 degrees, at one-quarter depth from surface 50 the blades have rotated 15 degrees; at one-half of the depth between surfaces 50 and 52 the blades have rotated 30 degrees, etc.

FIGS. 6 and 7 show apparatus for punching a slit in accordance with this invention into a partition valve 24. The silicone rubber disk (containing impregnated silicone oil) that is to become partition member 24 may be mounted in a jig 60, or otherwise mounted between casing portions 26, 28 on a catheter or the like. Triple-finned blade 62 is brought against the disk, while rotating as shown. Blade 62 is advanced through the opposed, major faces 50, 52 of the disk, being rotated by about 60 degrees as it advances between faces 50, 52, to cut the desired slit. Then, blade 62 is withdrawn from the newly-formed partition valve member 24.

Origin line 48, as well as helical slits 60, 62, 64, extend entirely through partition member 24 in a manner contrary, for example, to the disclosure of U.S. Pat. No. 4,626,245. When a catheter 12 or other elongated member is passed through partition valve member 24, it passes easily, with great tolerance, as to deviations in diameter of catheter 12, yet with good sealing retention of partition member 24 about catheter 12, and low catheter collapsing pressure exhibiting the advantages described above.

In accordance with this invention, both sides of partition member 24 define central, concave portions 71, 73. The entire helical slit occupies both concave portions, so that the thickness of the material through which the helical slit penetrates is less than the thickness of the material at peripheral portions 75 of partition 24. Specifically, partition member 24 may have a diameter of 0.3 inch, while the concave portions 71, 73 may each have a diameter of 0.12 inch, each of the concave portions being in concentric relation with partition 24. Partition 24 may have a maximum thickness of 0.07 inch, with the depth of each concave area 71, 73 being as particularly shown in FIG. 4. Preferably, each concave area defines a substantially spherical section. Thus, the concave faces defined in valve member 24 provide easier catheter manipulation through the valve, as well as less opportunity for collapse of the thin walled catheter which penetrates the valve, as described above.

When compressed, as by retention in the housing, the radial lines of the slit on the major faces of the partition valve may form arcs even though the original, cut lines are straight, due to compressive forces in the elastomeric valve. It follows that the original, cut lines on the major faces may be originally curved, if desired.

In the selection of a desired cross-sectional shape for slit 40 of this invention, the resistance of the valve to leakage of pressurized fluids will tend to increase as the angle subtended by the helical slit sections increases. In other words, an angle of 180 degrees between corresponding lines on opposed faces of partition member 24 (and that much twist provided to the respective helical slit sections) will tend to provide more sealing capability than a significantly lesser angle.

Similarly, the sealing power of partition member 24 will tend to increase with a reduction in the number of radii present in the slit cross-section. A straight line slit can therefore provide excellent sealing, especially when the helical section present twists by 60 degrees or more.

The above has been offered for illustrative purposes only, and is not intended to limit the scope of the invention of this application, which is as defined in the claims below.

That which is claimed is:

1. A valve which comprises an elastomeric partition member having a first face and a second, opposed face and adapted for securement in a housing, and a slit extending through said valve between the first and second faces, the improvement comprising, in combination:
    at least one of said faces defining a concave surface to reduce the central thickness of said partition member, said slit extending through said concave surface, said slit further defining a first line on said first face and a second line on said second face, said first line and said second line having a similar configuration but being in non-alignment with each other, with a generally helical slit section extending between said first line and said second line through said partition member.

2. The valve of claim 1 in which both said first face and said second face define concave surfaces between which said slit extends.

3. The valve of claim 1 in which said slit defines on said first face a first plurality of intersecting radii and on said second face a second plurality of intersecting radii, with said first plurality and said second plurality having a similar configuration but being in non-alignment with each other and with generally helical slit sections extending between said first plurality and said second plurality.

4. The valve of claim 3 in which the included non-alignment angle is between 10 and 180 degrees.

5. The valve of claim 3 in which the included non-alignment angle is essentially 60 degrees.

6. The valve of claim 3 in which said first and second plurality each define three intersecting, substantially equiangularly spaced radii.

7. The valve of claim 1 in which said partition member carries an impregnated lubricating oil.

8. The valve of claim 1 in which said partition member comprises a one-piece unitary member formed of silicone rubber.

9. A catheter sheath introducer including a housing, said housing including an elastomeric partition valve having a first major face and a generally parallel and opposing second major face, and a slit extending between said first and second major faces, the improvement comprising, in combination:
   at least one of said faces defining a concave surface to reduce the central thickness of said partition member, said slit extending through said concave surface, said slit also defining a first plurality of intersecting lines on said first major face and a second plurality of intersecting lines on said second major face, said first plurality and said second plurality having a similar configuration but being in nonalignment with each other, with generally helical slit sections extending between said first plurality and said second plurality.

10. The catheter sheath introducer of claim 9 in which both said first face and said second face define concave surfaces between which said slit extends.

11. A catheter sheath introducer as described in claim 9, in which the line at each major face defines three intersecting substantially equiangularly spaced radii.

12. A catheter sheath introducer as described in claim 9 in which said partition valve comprises a one-piece unitary member carrying an impregnating lubricating oil and being formed of silicone rubber.

13. A valve which comprises an elastomeric partition member having opposed major faces and secured in a housing, the improvement comprising, in combination:
   a slit extending through said partition valve between the major faces thereof, said slit defining a line at each major face, the respective lines at said opposed major faces defining an angle to each other, said slit defining at least one generally helical slit section between said lines on the major faces and within said partition valve, at least one of said major faces defining a concave surface to reduce the central thickness of said partition member, said slit extending through said concave surface.

14. The valve of claim 13 in which both of said major faces define concave surfaces between which said slit extends.

15. The valve of claim 14 in which said slit defines a line on each major face comprising a plurality of intersecting radii, each plurality of intersecting radii on each face having a similar configuration but being in nonalignment with each other, and with generally helical slit sections extending between the intersecting radii on each major face.

16. The valve of claim 15 in which the respective corresponding radii on the opposed major faces define an angle to each other of 10–180 degrees.

17. The valve of claim 16 in which said partition member carries an impregnated lubricating oil.

18. The valve of claim 17 in which said partition is formed of silicone rubber.

19. A medical instrument comprising a housing with means for providing a passage into the body, said housing further including a valve for receiving and sealing an elongated member which penetrates said valve, said valve comprising an elastomeric partition member having a first face and a second, opposed face, said partition member being secured in said housing, said partition member defining a slit extending through said valve between said first and second faces for receiving and sealing the elongated member, at least one of the faces of the partition member defining a concave surface to reduce the central thickness of said partition member with the slit extending through said concave surface, whereby the frictional resistance of the elongated member passing through the slit is reduced.

20. A medical instrument as defined by claim 19, in which both said first face and said second face of the partition member define concave surfaces between which said slit extends.

21. A medical instrument comprising a housing with means for providing a passage into the body, said housing further including a valve for receiving and sealing a elongated member which penetrates said valve, said valve comprising an elastomeric partition member having a first face and a second, opposed face, said partition member being secured in said housing, said partition member defining a slit communicating with said first and second faces for receiving and sealing the elongated member, at least one of the faces of the partition member defining a recessed surface to reduce the central thickness of said partition member with the slit extending through said recessed surface, whereby the frictional resistance of the elongated member passing through the slit is reduced.

* * * * *